United States Patent [19]
Kira et al.

[11] Patent Number: 5,919,171
[45] Date of Patent: Jul. 6, 1999

[54] MICROCATHETER

[75] Inventors: Kazuaki Kira, Kobe; Hiromi Maeda, Uji; Shuji Isozaki, Hadano, all of Japan

[73] Assignee: Kanegafuchi Kagaku Kogyo Kabushiki Kaisha, Osaka-fu, Japan

[21] Appl. No.: 08/776,316

[22] PCT Filed: Aug. 2, 1995

[86] PCT No.: PCT/JP95/01533

§ 371 Date: Jan. 30, 1997

§ 102(e) Date: Jan. 30, 1997

[87] PCT Pub. No.: WO96/04033

PCT Pub. Date: Feb. 15, 1996

[30] Foreign Application Priority Data

Aug. 3, 1994 [JP] Japan ................................. 6-202801
Jun. 29, 1995 [JP] Japan ................................. 7-188314

[51] Int. Cl.⁶ ........................................................ A61M 5/00
[52] U.S. Cl. ........................................... 604/264; 604/280
[58] Field of Search ....................................... 604/264, 280, 604/96, 164, 158

*Primary Examiner*—Wynn Wood Coggins
*Assistant Examiner*—N. Kent Gring
*Attorney, Agent, or Firm*—Armstrong, Westerman, Hattori, McLeland & Naughton

[57] ABSTRACT

A microcatheter for infusion in which a tip portion of its shaft 2 comprises a porous tubular structure 3 having no communicating pores is provided. It can be inserted into fine peripheral blood vessels along a guiding wire and/or on a blood stream, and thus a contrast medium, a curative drug, an embolismic substance or the like can be infused in the desired portion.

4 Claims, 2 Drawing Sheets

MICROCATHETER

TECHNICAL FIELD

The present invention relates to a microcatheter for infusion, which is inserted into fine peripheral blood vessels for diagnosis or treatment of blood vessels or internal organs.

BACKGROUND ART

Medical treatment in which a catheter inserted into a blood vessel transcutaneously is led to an internal organ such as a brain, a heart or some of abdominal organs to thus administer or infuse therethrough a proper curative drug, an embolismic substance or a contrast medium has been carried out. In recent years, in view of never-ending progress of medicine, it has become necessary to infuse such curative drug, embolismic substance or contrast medium into still finer peripheral blood vessels and now desired is development of a microcatheter which is capable of insertion into such finer peripheral blood vessels.

With a conventional catheter for infusion, it is a usual practice to have it led to an affected part along a guiding wire preset thereto.

Also developed is a method of making a tip portion of a catheter pliable and, if necessary, bulged so as to make the catheter movable on a blood stream. As a typical example of such catheter is Mallinckrodt Balt Magic Catheter (Trade Name) made by Mallinckrodt Medical Inc.

Meanwhile, as a catheter with a part of its shaft comprising a porous structure, there is exemplified, for example, a catheter with its tip portion made porous lest a blood vessel should be injured thereby, disclosed by Japanese Patent Laid-Open Publication No. 2-142576, an intra-abdominal retention tube made up of a porous part and a nonporous part for the improved adaptability to the form of the abdominal cavity, disclosed by Japanese Patent Laid-Open Publication No. 2-107268 for decreasing a risk of injury to the internal wall of the abdomen when it is retained in the abdominal cavity, a catheter made of polytetrafluroethylene (PTFE) and comprising a porous part and a solid part such that a proper flexibility is attained, disclosed by Japanese Patent Laid-Open Publication No. 60-51912. Also proposed are catheters by Japanese Patent Laid-Open Publication No. 60-129055 and No. 61-247476, each with its normally open tip portion having micro-pores communicating the inside with the outside of a porous tube closed, and when a thrombus-dissolving agent is infused through a proximal portion and the infused agent is caused to be discharged gradually through the side wall of the porous tip portion.

The conventional catheter to be led to an affected part of a blood vessel by the use of a guiding wire is usable without any clinical problem if its outer diameter is relatively large (e.g. 1.5 to 4 mm). Its shaft is however is large in diameter and solid compared with a blood vessel, hence it is rather difficult to insert into fine peripheral blood vessels.

With the rapid development of diagnostic devices such as MRI and CT in the field of neurosurgery, blood vessel diseases (aneurysm, tumor, arteriovenous malformation etc.) in mesencephalic cerebral arteries, basilar artery, anterior communicating artery, posterior communicating artery, anterior cerebral artery, posterior cerebral artery etc. are now readily detectable. Craniotomy of blood vessel diseases in such parts is often infeasible depending on the parts affected due to too high physical burden on a patient or too high probability of complication and operation is possibly infeasible depending on the parts affected. It is, therefore, strongly desired lately to enable insertion of a microcatheter for infusion for detailed diagnosis and treatment. With a conventional catheter which can be readily inserted into common carotid artery, external carotid artery, internal carotid artery etc., it is often difficult to insert it into the peripheral portions thereof, the time required for insertion into such portions is likely too long and often such insertion is infeasible depending on the conditions of a patient.

The catheter moved on a blood stream has its pliable tip portion made of a polyurethane elastomer and a silicone rubber either alone or in combination, hence this pliable tip portion is low in physical strength and resistance to solvents and has a defect of such portion being subject to damage during infusion of a contrast media or its tip portion being dissolved depending on the kind of a solution infused.

Especially, it is often the case that the pressure which is imposed upon the catheter inner wall is about 100 PSI or even more when a contrast medium is infused, this being too high for such catheter to withstand.

Further, it is necessary to increase a wall thickness of a tube for insufficient strength because of its material being poor in physical strength, this resulting in a decreased inner diameter of the catheter. Moreover, since the material of the tip portion is elastic, this portion tends to elongate in the axial direction of its shaft and in the case of a fine peripheral blood vessel, the tip portion elongates and is broken as a guiding wire is worked therein, this resulting in a fault of the guiding wire not usable for helping insertion of a catheter into a fine peripheral blood vessel.

Meanwhile, conventional catheters with a part of their shaft being of porous structure so far developed are those which are safe from injuring the inner wall of a blood vessel with their tip portion pliable or which are capable of gradually discharging a curative drug solution through the portion of the porous structure, but no catheters possibly inserted into a fine peripheral blood vessel have been developed yet.

The catheter disclosed by the above-mentioned Japanese Patent Laid-Open Publication No. 2-142576 is not a microcatheter for infusion usable for fine peripheral blood vessels, being simply with its tip portion made pliable to be safe from injuring the inner wall of a blood vessel as is apparent from the "Object of the Invention" and from the description "those 1.5 to 3 mm in outside diameter, 1.0 to 1.8 mm in inside diameter and 0.3 to 0.6 mm in wall thickness are practical." The catheter disclosed by the above-mentioned Japanese Patent Laid-Open Publication No. 2-107268 is an intra-abdominal retention tube being pliable to be readily adaptable to the form of abdominal cavity when it is retained therein, and the excessive pliability disturbs its use as a microcatheter for insertion into fine peripheral blood vessels. Moreover, the catheter disclosed by the above-mentioned Japanese Patent Laid-Open Publication No. 60-51912 is comprised of a solid part and a porous part without any device for the insertion into fine peripheral blood vessels, and therefore, it is not used as a catheter for infusion for such fine peripheral blood vessels.

Hence, the present invention is to provide a microcatheter for infusion for solving the aforementioned problems and infusable into still finer peripheral blood vessels.

After intensive series of studies for the accomplishment of the aforementioned object, the present inventors have found that a microcatheter for infusion in which a tip portion of its shaft to be inserted into fine peripheral blood vessels is made pliable by the use of a porous wall tube having no communicating pores therein and is made smaller in outer diameter as well as wall thickness so as to be insertable into fine peripheral blood vessels by the aid of a guiding wire and/or on a blood stream and is imparted enough physical strength to withstand the pressure required for infusion.

DISCLOSURE OF THE INVENTION

The present invention relates to a microcatheter for infusion in which a tip portion of its shaft comprises a porous tubular structure having no communicating pores, a length of said porous tubular structure being from 20 to 60 cm, an outside diameter thereof being from 1 to 0.3 mm and a wall thickness thereof being from 0.2 to 0.05 mm.

The present invention further provides a microcatheter with its shaft outside diameter increasing from its tip portion toward its proximal portion continuously or stepwise, another microcatheter with a pore ratio of its porous structure decreasing from its tip portion toward its proximal portion continuously or stepwise, and still a further microcatheter with an expansible member in a tip portion of its shaft.

In the present invention, the shaft means a tubular structure portion except a connector of the catheter proximal portion, while the tip portion means a portion remote from the catheter proximal portion, which is to be inserted into a fine blood vessel.

The microcatheter of the present invention comprises a porous tubular structure with no communicating pores therein in a tip portion of its shaft and the tip portion is made small in outside diameter as well as wall thickness and is also pliable, hence it can be easily inserted therethrough into fine peripheral blood vessels of a brain, a heart or the like for infusion of a curative drug and the like.

BEST MODE FOR CARRYING OUT THE INVENTION

Figure 1:
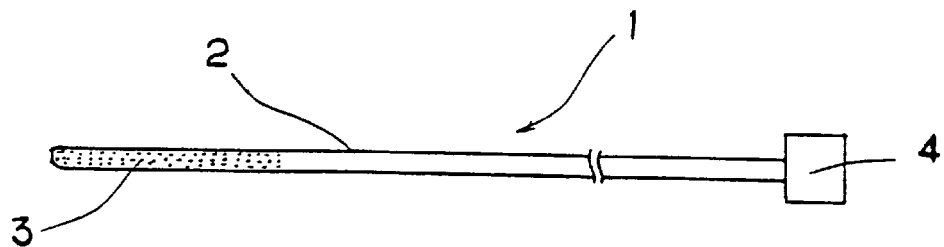
FIG. 1 is a schematic illustration of an example of the present invention.

A highpolymer tubular structure can be improved in pliability by making it porous. In the present invention, pliability is defined as a ratio of deformation of a tubular structure to a force applied thereto in the circumferential direction. That is, a tubular structure is appreciated as pliable if its deformation is large even when a force applied thereto in the circumferential direction is small.

The pliability referred to in the present invention is not affected by elongation resulting from a pulling force applied to the tubular structure in the axial direction. That is, the porous tubular structure referred to in the present invention, which is readily deformed by the force applied in the circumferential direction, is not substantially elongated by the pulling force in the axial direction.

Normally, pliability of a porous tubular structure increases with an increase in a pore ratio of the porous tubular structure. Hence, with a given material, its pliability is changeable by changing its pore ratio.

The pore ratio (%) is determinable by the following formula:

(Volume of pores in a tubular wall of a tubular structure/Volume of the tubular wall of the tubular structure)×100%.

The volume of pores in the tubular wall of tubular structure may be determined as follows.

{(Volume of the tubular wall of the tubular structure−Weight of the tubular structure)/Specific gravity of a material of the tubular structure)}

The pore ratio of the porous tubular structure of the catheter of the present invention is not particularly limited if it is enough to provide the required pliability. For enough pliability, the pore ratio is preferred to be in a range of from 25 to 95%. For well balanced impartation of pliability and physical strength, it is still more preferable to have the pore ratio in a range of from 50 to 90%.

As to the highpolymer materials forming such porous tubular structure, there is no particular limitation, either, if it is molded to a porous tubular structure and satisfies safety and properties required for catheters such as physical strength. As such high polymer materials, there are included, for example, polytetrafluoroethylenes (PTFE), polyethylenes, polystyrenes, polyvinyl chlorides and polyurethanes, which may be used alone or in combination of two or more. It is, however, preferable to use the PTFE if it is desired to have an outside diameter of the porous tubular structure small, to make it pliable but with no elongation and also to make the tubular wall thin.

The pores formed in the porous tubular structure of the present invention are not communicating from the inside to the outside of the tubular wall lest an infused curative drug, embolismic substance, contrast medium etc. should leak through the porous tubular wall. As typical examples of the curative drug, embolismic substance, contrast medium etc., there are included, for example, thrombus-dissolving agents such as urokinase and tissue-type plasminogen, carcinostatic agents, embolismic agents containing carcinostatic agents, embolismic substances against aneurysm such as metal coil and ethylene-vinyl alcohol copolymers (trade name: EVAL), embolismic substances against cerebral arteriovenous malformation such as ethylene-vinyl alcohol copolymers (PVA), silk yarn and coil. Such curative drugs, embolismic substances and control media are either liquid or solid but solid ones are often infused as dissolved with a liquid such as a physiological saline solution. It is also often the case that a curative drug or embolismic substance is infused after infusion of a contrast medium using the same microcatheter.

The microcatheter of the present invention has a porous tubular structure having a length of from 20 to 60 cm, hence it is highly necessary to ensure against leakage of a curative drug, an embolismic substance, a contrast medium and/or a liquid used for infusion thereof. The porous tubular structure of the present invention has no communicating pores opening from the inside to the outside of the tubular wall. This means that there is substantially no risk of leakage, through the porous tubular wall, of a curative drug, an embolismic substance and a contrast medium when those are infused. In the present invention, the word "no communicating pores" should be construed as such if such leakage does not take place substantially, even if a few communicating pores are observed through e.g. an electronic microscope, and such case, needless to say, being included in the present invention.

For improving the blood compatibility and/or ensuring against leakage of an infused liquid, a porous tubular structure may be combined with a non-porous thin-walled inner or outer tube or cover.

The porous tubular structure may be formed by various methods such as an expansion molding method, a stretching method, a pore-making agent method and a laser beam method. The pore ratio of the porous tubular structure is adjustable by means of an expansion ratio, a stretching ratio, an amount of the pore-making agent used and/or a laser beam dosage. If formation of communicating pores is inevitable by any of such methods, the communicating pores have to be eliminated by the use of some solvent capable of dissolving the tube material, or by heating, or laminating with a material having no communicating pores, or by impregnation or coating with the same or a different resin to close such communicating pores, if any.

The microcatheter of the present invention has a shaft whose tip portion comprises a porous tubular structure. That is, the tip portion to be inserted into a fine peripheral blood vessel with the pushability of the microcatheter of the present invention retained is made porous and the rest of the shaft portion is substantially nonporous.

The material of the rest of the shaft portion may be the same as or different from that of the porous tubular structure. For optimization of pushability etc. of the microcatheter, however, it is advisable to use a different material for an increased scope of selection. The tip of the shaft is opened for discharge of some contrast medium, curative drug, embolismic substance or the like.

The length of the porous tip portion is preferably in a range of from 20 to 60 cm, more preferably in a range of from 30 to 50 cm with the location and length of the peripheral blood vessel into which the catheter is inserted as well as its workability taken into consideration.

In order to insert the microcatheter into a fine peripheral blood vessel with its pushability retained, it is desirable to have the outside diameter of the shaft portion to be increased from the tip end toward the proximal portion continuously or stepwise. In order to insert the microcatheter into a fine peripheral blood vessel with its pushability retained, it is desirable to have the pore ratio of the porous tubular structure decreased from the tip end toward the proximal portion continuously or stepwise.

When the microcatheter of the present invention is inserted into a fine peripheral blood vessel, the outside diameter of the tip portion of the porous tubular structure is required to be in a range of from 1 to 0.3 mm, more preferably in a range of from 0.8 to 0.4 mm. The tubular wall thickness of the tip portion of the porous tubular structure of the catheter of the present invention is preferably smaller if the physical strength required for the catheter is retained, since the cavity thereof is increased, workability of a guiding wire is improved and the infusion rate is increased. These taken into consideration, the thickness of the tubular wall of the tip portion of the porous tubular structure is preferably in a range of from 0.2 to 0.05 mm, more preferably in a range of from 0.15 to 0.07 mm.

As to the proof pressure of the shaft of the catheter of the present invention, there is no particular limitation if it is enough to withstand the pressure imposed during infusion of some contrast medium, curative drug, embolismic substance or the like. The internal pressure imposed during infusion depends on the diagnosis and the curative methods but when a contrast medium is infused, it often becomes high. Hence, the proof pressure is preferably not less than 200 PSI, more preferably it is safe from rupture even at 1,000 PSI.

When the microcatheter is inserted with ease on a blood stream into a fine peripheral blood vessel, it is desirable to provide an expansible member in the tip portion of the shaft. As to the expansible member, there is no particular limitation if its outside diameter is large to produce a sufficient resistance to the blood stream and is smaller than the inside diameter of the fine blood vessel into which it is inserted. If the blood vessel to be inserted into is fine, the expansible member is preferred to be 10 to 100 μm larger in outside diameter than the shaft of the catheter. In order to adjust the resistance to the blood stream for smooth insertion of the catheter at the predetermined location in the blood vessel, it is preferred that the expansible member is a balloon and more preferred that inflation and deflation of this balloon are controllable at a connector portion.

The catheter of the present invention will be explained in greater detail with reference to the accompanying drawings.

FIG. 1 is a schematic illustration of a microcatheter of the present invention, wherein the microcatheter 1 has a tip portion of a shaft 2, comprising a porous tubular structure. The numeral 4 represents a connector portion, which is outside a human body when the catheter is in clinical use and is served as an inlet for a guiding wire, a curative drug, an embolismic substance, a contrast medium and the like. The connector portion may as well be a branched tube.

Figure 2:
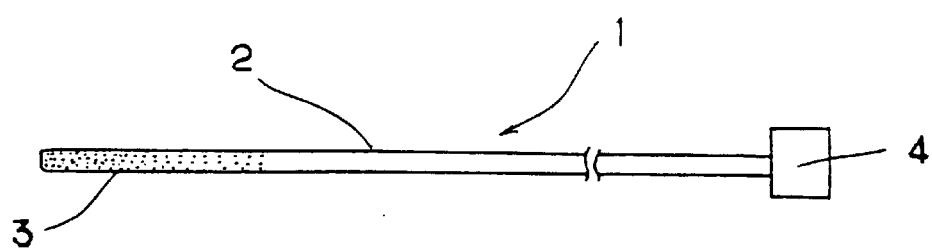
FIG. 2 is a schematic illustration of another example of the present invention.

A microcatheter 1 shown in FIG. 2 has a pore ratio of a porous tubular structure 3 decreased from its tip portion toward the proximal portion continuously, in the microcatheter shown in FIG. 1.

Figure 3:
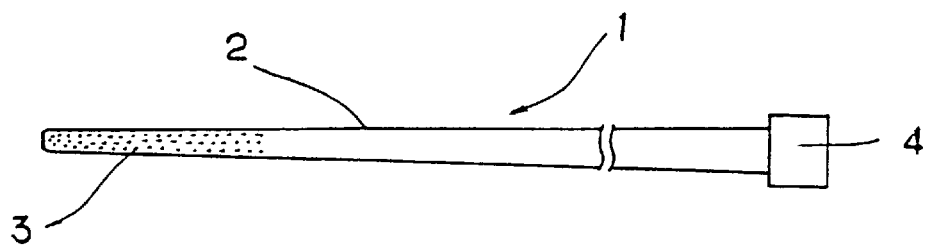
FIG. 3 is a schematic illustration of still another example of the present invention.
Figure 4:
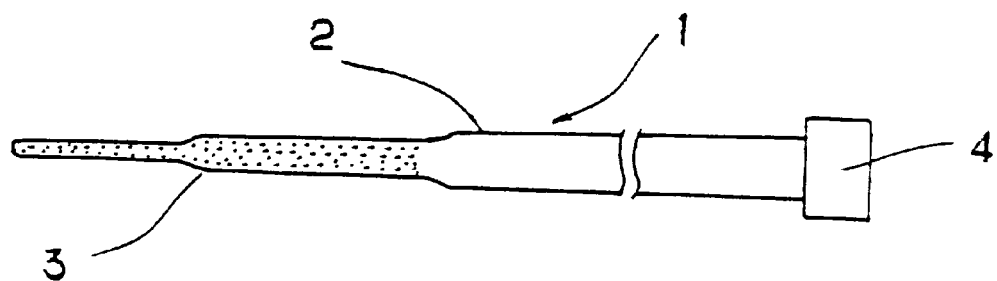
FIG. 4 is a schematic illustration of a separate example of the present invention.

A microcatheter 1 shown in FIG. 3 or FIG. 4 has an outside diameter of the shaft 2 increased from the tip portion to the proximal portion continuously (FIG. 3) or stepwise (FIG. 4). In FIG. 4, portions where the outside diameter varies stepwise are rounded for smoother variation.

Figure 5:
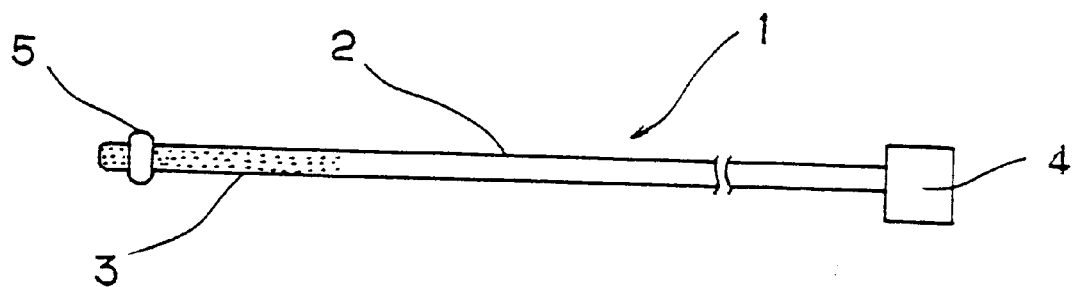
FIG. 5 is a schematic illustration of a still separate example of the present invention.

A microcatheter 1 shown in FIG. 5 is provided with an expansible member 5 somewhat larger in outside diameter than the aforementioned porous tubular structure 3 in the vicinity of the tip portion thereof. The expansible member 5 acts as resistance to a blood stream and this resistance produces a propulsive force which helps movement with ease of the microcatheter 1 on a blood stream to the predetermined location.

Industrial Applicability

The microcatheter of the present invention has a shaft whose tip portion comprises a porous tubular structure with no communicating pores therein, the tubular structure is small in outside diameter as well as wall thickness and is very pliable, hence it can be inserted with ease into fine peripheral blood vessels along a guiding wire and/or on a blood stream.

Further, the microcatheter is provided with an expansible member at the tip portion of the shaft, and thus, it is easily moved on a blood stream, hence it can be inserted with ease into fine peripheral vessels of a brain, a heart or the like.

Moreover, since the microcatheter of the present invention is made of a porous structure with no communicating pores therein, hence a contrast medium, a curative drug, an embolismic substance or the like can be effectively infused into peripheral blood vessels without any risk of leakage through the wall of the porous tubular structure.

We claim:

1. A microcatheter for infusion wherein a tip portion on a shaft comprises a porous tubular structure having no communicating pores opening in the direction from inside to outside on said porous tubular structure, and a length of said porous tubular structure is from 20 cm to 60 cm, an outside diameter of said porous tubular structure is from 1 mm to 0.3 mm and a wall thickness of said porous tubular structure is from 0.2 mm to 0.05 mm.

2. A microcatheter as defined in claim 1, wherein an outside diameter of the shaft increases from its tip portion toward a proximal portion continuously or stepwise.

3. A microcatheter as defined in claim 1 or 2, wherein a pore ratio of the porous tubular structure decreases from its tip portion toward its proximal portion continuously or stepwise.

4. A microcatheter as defined in claim 1 or 2, wherein an expansible member is provided at the tip portion of the shaft.

* * * * *